United States Patent
Duren

[19]

[11] Patent Number: 5,988,876
[45] Date of Patent: Nov. 23, 1999

[54] METHOD FOR MEASURING TEMPERATURE OF AN AIRFLOW FOR AN INFLATABLE THERMAL DEVICE

[75] Inventor: Albert Van Duren, Chaska, Minn.

[73] Assignee: Augustine Medical, Inc., Eden Prairie, Minn.

[21] Appl. No.: 09/177,042

[22] Filed: Oct. 20, 1998

Related U.S. Application Data

[62] Division of application No. 08/893,175, Jul. 15, 1997, Pat. No. 5,876,428.

[51] Int. Cl.⁶ .............................. G01K 1/14; G01K 13/02
[52] U.S. Cl. ............................................. 374/148; 374/143
[58] Field of Search ..................................... 374/148, 147, 374/143

[56] References Cited

U.S. PATENT DOCUMENTS

| Re. 27,354 | 5/1972 | Wiebe et al. | 374/142 |
|---|---|---|---|
| 2,190,383 | 2/1940 | Newman | 607/105 |
| 2,190,384 | 2/1940 | Newman | 607/105 |
| 4,138,890 | 2/1979 | Brown | 374/148 |
| 4,398,535 | 8/1983 | Guibert | 128/399 |
| 4,572,188 | 2/1986 | Augustine et al. | 128/380 |
| 4,647,219 | 3/1987 | Figler et al. | 374/1 |
| 4,989,456 | 2/1991 | Stupecky | 73/863.53 |
| 5,060,655 | 10/1991 | Rudolph | 128/716 |
| 5,111,827 | 5/1992 | Rantala | 128/719 |
| 5,277,196 | 1/1994 | Hankinson et al. | 128/725 |
| 5,300,098 | 4/1994 | Philipot | 607/96 |
| 5,300,101 | 4/1994 | Augustine et al. | 607/107 |
| 5,300,102 | 4/1994 | Augustine et al. | 607/107 |
| 5,324,320 | 6/1994 | Augustine et al. | 607/107 |
| 5,405,371 | 4/1995 | Augustine et al. | 607/107 |
| 5,693,079 | 12/1997 | Van Duren | 607/107 |
| 5,876,428 | 3/1999 | Van Duren | 607/107 |

OTHER PUBLICATIONS

"Procedure To Check Output Temperature Of Warm Touch® Model 5000 And Model 5100 Warming Units", Malinckrodt Medical, Inc., Anesthesiology Division, Technical Bulletin No. WT202, Mar. 3, 1993.

*Primary Examiner*—Diego Gutierrez
*Assistant Examiner*—Stanley J. Pruchnic, Jr.
*Attorney, Agent, or Firm*—Gray Cary Ware Freidenrich

[57] ABSTRACT

Temperature of an airflow for an inflatable thermal device is measured near where the temperature is delivered to the device through an air hose by a method that simulates the frictional airflow resistance of the device. According to the method, an airflow resistor is receivable on that end of an hose that connects to an inflatable thermal device. The airflow resistor has a defined airflow resistance that corresponds to the airflow resistance of the inflatable thermal device.

7 Claims, 5 Drawing Sheets

METHOD FOR MEASURING TEMPERATURE OF AN AIRFLOW FOR AN INFLATABLE THERMAL DEVICE

This is a Divisional of U.S. patent application Ser. No. 08/893,175, filed Jul. 15, 1997, now U.S. Pat. No. 5,876,428 entitled "Apparatus and Method for Simulating an Inflatable Thermal Blanket to Test an Air Source".

BACKGROUND OF THE INVENTION

1. Field of the Invention

The invention concerns the simulation of an inflatable thermal blanket for testing an air source used to provide thermally-controlled, pressurized air to the blanket. More particularly, the invention concerns an inflatable thermal blanket simulator that includes an airflow resistor. When fitted over the end of an air hose, the simulator presents the apparent airflow resistance of an inflatable thermal blanket to an air source that is coupled to the other end of the air hose.

2. Description of the Related Art

Inflatable thermal blankets that operate by convecting temperature-controlled air are well-established clinical tools that are used, for example, to treat hypothermia. Such blankets have been produced and sold by AUGUSTINE MEDICAL, INC., the assignee of this application, and are gaining a gathering acceptance as evidenced by increases in sales every year since their introduction in 1989 by the assignee. These blankets are described in detail in, for example. U.S. Pat. Nos. 4,572,188; 5,300,101; 5,300,102; 5,324,320; and 5,405,371, among others. All of these patents are assigned to AUGUSTINE MEDICAL, INC., and are incorporated into this application by this reference.

Air sources for inflatable thermal blankets are well known. One is described, for example, in U.S. patent application Ser. No. 08/525,407, filed Sep. 8, 1995, and assigned to AUGUSTINE MEDICAL, INC., the assignee of this patent application. Typical air sources are represented, for example, by the Bair Hugger® Model 500/OR and Model 505 products, both available from AUGUSTINE MEDICAL, INC., the assignee of this application.

Commercially available air sources used to provide temperature-controlled, pressurized air to inflatable thermal blankets include a heater or cooler and a blower unit which operate to provide a steady stream of temperature-conditioned air at a given flow rate. The temperature-conditioned air is ducted from the air source to an inflatable thermal blanket which disperses the temperature-controlled air around a patient in order to raise or lower the core body temperature of the patient. The temperature of the air which reaches the inflatable thermal blanket is a function of several factors including, but not limited to: 1.) the heating or cooling capacity of the temperature-conditioning unit; 2.) the blower capacity; 3.) the length and thermal conductivity of the duct (typically, an air hose) between the air source and the inflatable thermal blanket; and, 4.) the airflow resistance of the inflatable thermal blanket.

The thermal characteristic of an airflow leaving an air source is generally controlled by continuously sensing the temperature of the airflow and adjusting power provided to the heating or cooling unit to maintain the temperature at a constant setting. The temperature of the airflow at the end of the air hose that couples to the inflatable thermal blanket (the "distal end" of the air hose), however, depends greatly on the time that the air remains within the air hose between the air source and the inflatable thermal blanket. This time is generally referred to as "residence" time. The most important variable that affects residence time is the airflow resistance imposed by the inflatable thermal blanket.

As is known, various inflatable thermal blanket configurations are available, each configuration designed to accomplish a particular clinical or therapeutic purpose, and each presenting its own airflow resistance, which is likely to be different than the airflow resistance presented by a different, or no, inflatable thermal blanket.

None of the currently available air sources are designed to sense either the external resistance to which they are attached or the temperature at the distal end of an air hose. Therefore, calibration and verification of the airflow temperature available at the distal end of the air hose, which is the airflow provided to the inflatable thermal blanket, should be performed with the air source operating into the same resistive load as that which is presented by one or more typical inflatable thermal blankets Calibration or verification could, of course, be performed by connecting an inflatable thermal blanket at the distal end of the air hose and inserting a temperature measuring device into the airflow; however, this method requires a large space, the sacrifice of an inflatable thermal blanket, and the use of external equipment. This method also suffers from the inability to control uniformly "fin effect" losses which occur through the temperature measuring device.

Accordingly, a need exists for provision of means useful for measurement of the temperature of an airflow delivered to an inflatable thermal blanket. Preferably such a means should present a test condition approximating the actual airflow resistance of an inflatable thermal blanket.

SUMMARY OF THE INVENTION

This invention is based on the inventor's critical observation that a well-characterized, frictional airflow resistance can be presented in a very compact form by a porous structure receivable over the distal end of an air hose. The inventor provides, with his invention, a portable, inexpensive, self contained airflow resistor that incorporates the porous structure and presents a well-characterized, frictional airflow resistance that closely mimics the resistance of an inflatable thermal blanket.

An objective of this invention is therefore to provide a frictional airflow resistor receivable over the distal end of an air hose for simulating an inflatable thermal blanket to measure the temperature of pressurized air delivered by an air source.

A further objective is to provide a method for measuring the inlet temperature presented to an inflatable thermal blanket across an airflow resistor that simulates the resistance of the inflatable thermal blanket.

Another objective is to provide for measurement of the pressure drop across the airflow resistor.

Yet one more objective is to compute airflow through the resistor by way of the proportional relationship of flow to pressure.

These objectives are achieved by an airflow resistor that behaves exactly as an inflatable thermal blanket in that its resistance losses are all frictional and vary parabolically with respect to flow.

Moreover, it is beneficial that the design of the airflow resistor permits the construction of inflatable thermal blanket simulators having different, but well-defined, resistance characteristics to simulate the operation of different types of inflatable thermal blankets.

The achievement of these and other objectives and significant advantages by the invention will become evident when the following detailed description is read with reference to the below-described drawings.

DETAILED DESCRIPTION OF THE PREFERRED EMBODIMENTS

Figure 1:
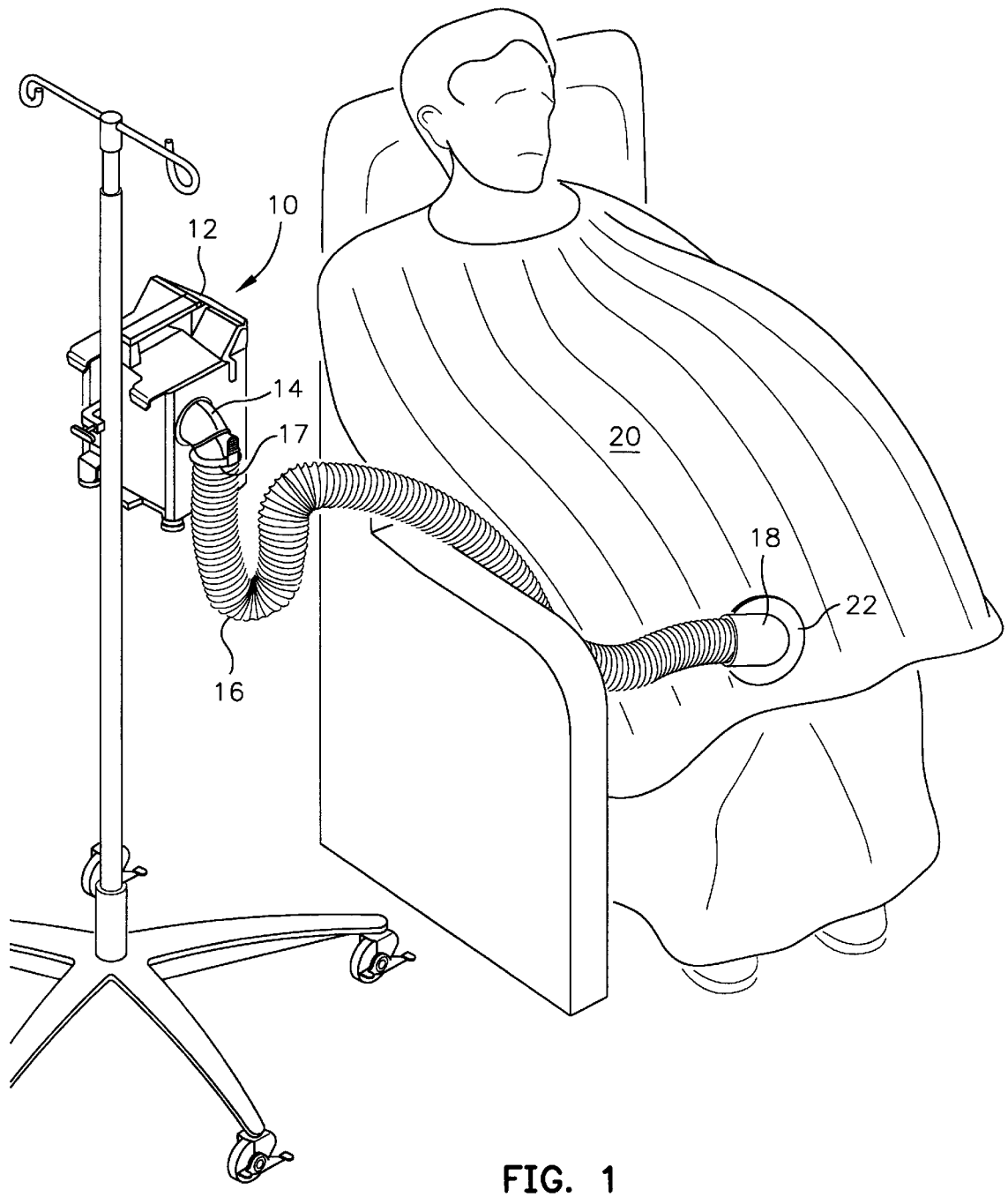
FIG. 1 illustrates a convective system for controlling the temperature of a patient by means of an inflatable thermal blanket.
Figure 2:
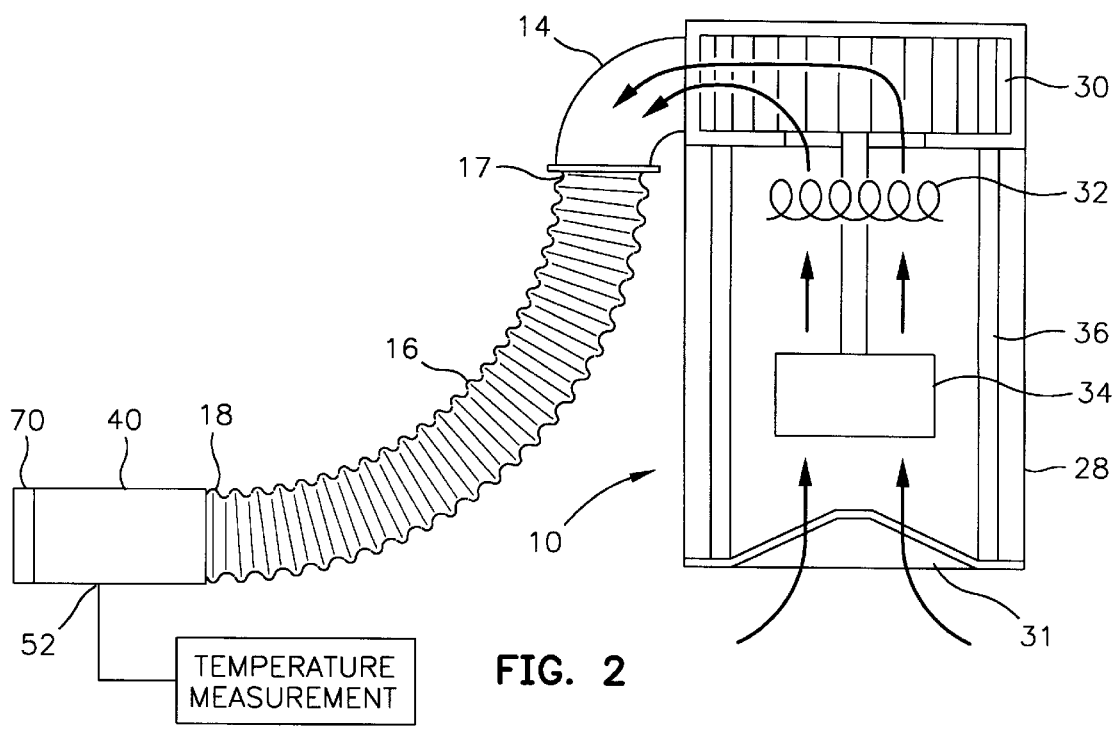
FIG. 2 is a schematic diagram illustrating use of inflatable thermal blanket simulator that embodies the apparatus of this invention in combination with an air source and a flexible air hose.

Refer now to the figures where similar elements or features are indicated by the same reference numerals throughout the drawings. In particular, FIGS. 1 and 2 show components of a system for convectively controlling the core temperature of a human body. These components are described in terms of temperature elevation in that they operate to raise the core temperature of a human body to promote treatment of hypothermia, or the healing of wounds, for example. It should be understood that with a change to a means for conditioning airflow temperature, the description could apply as well to a cooling system used to treat, for example, heat stroke or heat exhaustion.

A system for raising the core temperature of a person includes an air source 10 that delivers heated, pressurized air through a coupling 14 to which a flexible air hose 16 is attached at one end 17 (the "proximal" end). The second ("distal") end 18 of the air hose 16 is coupled to an inflatable thermal blanket 20 by way of inflation port cuff 22. The air source 10 includes a control panel 12 that provides buttons or similar user-operated means to select airflow temperature. In some air sources, the airflow rate is fixed, in others it may be variable. The essential elements of the air source 10 that are controlled by way of the control panel 12 are shown in FIG. 2. In FIG. 2, the air source 10 includes a low-noise air blower unit (also "blower unit") having a casing 28 that contains a blower 30 powered by an electric motor 34. The blower 30 can comprise, for example, a squirrel cage blower. This type of blower typically has a short cylinder with a plurality of fan blades that are positioned around the circumference of the cylinder. The blower 30, operated by the motor 34, draws ambient air into the casing 28 through an inlet 31 and creates an airflow that continues up, into and through the coupling 14. The airflow is heated by a heater 32, which may comprise a resistive heating coil. The power radiated by the heating coil 32 may be controlled from the control panel 12. In some units provision may be made for varying motor speed. Control of the speed of the blower unit 30 controls the rate of the airflow delivered through the coupling 14; control of the power delivered to the heater 32 controls the airflow's temperature.

In FIG. 2, measurement of the temperature of the airflow delivered by the air source 10 through the air hose 16 is supported by provision of a simulator 40 that is slidably received on the distal end 18 of the air hose 16. The simulator 40 includes an airflow resistor that operates by frictionally impeding the airflow as it exits the distal end 18, which closely mimics the effect of an inflatable thermal blanket represented by the simulator 40.

Figure 4:
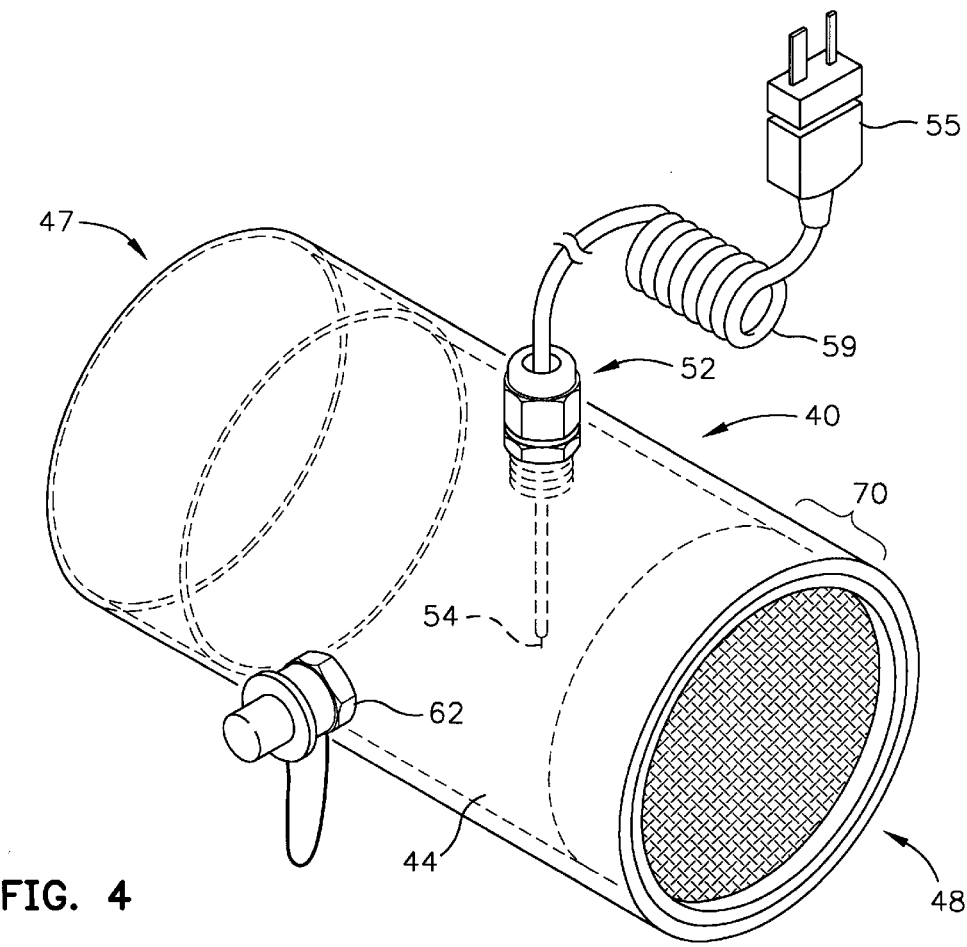
FIGS. 3, 4, and 5 illustrate various construction details and elements of the simulator of FIG. 2, which includes an airflow resistor.
Figure 3:
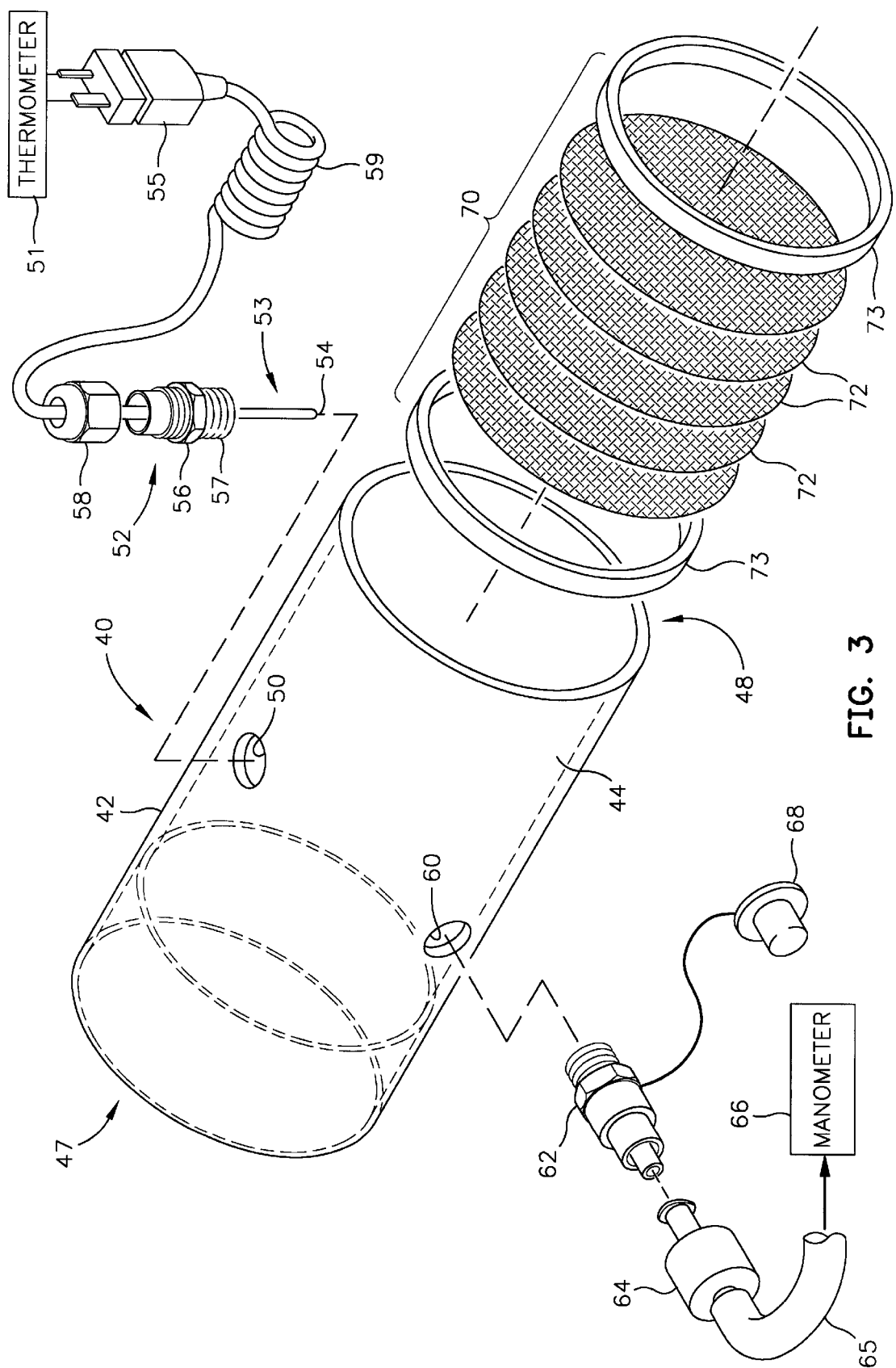

One embodiment of the simulator 40 is illustrated in FIGS. 3 and 4. It should be understood that this embodiment is only representative of many possible instantiations of an inflatable thermal blanket simulator that incorporates an airflow resistor.

With specific reference to FIGS. 3 and 4, the simulator 40 includes a conduit 42 in the particular form of a right cylindrical tube. The conduit has an outer surface 44, an inner surface 46, and two ends, a first end being denoted by 47 and a second end by 48. The cylindrical tubular structure of the conduit 42 enables it to contain an airflow between the two ends 47 and 48. A hole 50 opens through the outer surface 44 into the interior of the conduit 42. The hole 50 is preferably a circular threaded hole that is placed to position a temperature sensor in the conduit 42 where it will sense the temperature of the air flowing through the conduit 42. The temperature sensor, indicated generally by 52, includes a thermocouple cable 53 having a thermocouple bead 54 at one end and a thermocouple coil cable 59 near another end. A plug 55 adapts the temperature sensor 52 for being conventionally electrically connected to a measuring/recording thermometer 51 such as a Fluke® model 51K/J or other, equivalent device. The thermocouple bead 54 is kept in place by an adjustable pigtail fitting including a strain relief device 56 having a threaded part 57 for engaging the threads of the circular hole 50. A nut 58 squeezes the strain relief unit 56 around the thermocouple cable 53.

If it is desired to also measure the pressure drop between the interior of the conduit 42 and the ambient air, a second circular, threaded burr-free hole 60 may be provided. In the preferred embodiment, access through the burr-free hole 60 is provided by a port 62 with a threaded lower portion. When not used, the port 62 is sealed by a plug 63. FIG. 3 shows the male luer fitting 64 of a pressure measurement tube 65 retained on the port 62. The tube 65 is conventionally connected to a pressure measuring/recording device 66, such as a manometer. The second hole 60 and its associated port 62 are optional and are not necessary to the practice of the invention. However, when the second hole 60 is provided, it should be located away from the first hole 50 in order to avoid measuring the effects of turbulence caused by the temperature sensor 52. Preferably the second hole 60 is arcuately displaced from the first hole 50 by, for example, 90°.

An airflow resistor 70 according to the invention is composed of a plurality of circular mesh screens 72 that are arranged in sequence between two circular rings 73. The mesh screens may be cut from for example, 14×16×0.013" aluminum screen which exhibits a substantially rectangular grid of fourteen wires by sixteen wires per square inch, with the diameter of the wires being 0.013 inches. The circular mesh screens 72 are arranged so that the parallel strands in one screen are offset by rotation with respect to the corresponding strands of a preceding (or succeeding) screen. The rotation may be, for example, through an arc of 45°. The number of mesh screens 72 is selected to give a pressure drop that is appropriate to a particular inflatable thermal blanket. For example, the Model 300 Full Body Inflatable Thermal Blanket available from AUGUSTINE MEDICAL, INC. is well simulated by eleven sections of mesh screen 72. The relation of the number of screens required to present a particular airflow resistance representing a particular inflatable thermal blanket produced by AUGUSTINE MEDICAL, INC. is given in Table I.

In its preferred embodiment and best mode, the simulator 40 may comprise a 6-inch length of clear polycarbonate pipe having an outside diameter of 2.5 inches and an inside diameter of 2.25 inches. The first (proximal) end 47 of the pipe is machined on its inner surface to accept the nozzle from an air hose. A temperature sensor such as the thermocouple bead 54 is retained on the pipe by the means described above, with the thermocouple wire entering the pipe at a right angle. The second (distal) end 48 of the pipe contains the airflow resistor 70 that includes a preselected number of circular mesh screens 72. The mesh screens are retained between two circular rings 73 that are, preferably, made of polycarbonate. The inventor has constructed airflow resistors that have the structure and function of the airflow resistor 70 and that can be handled as integral units by gluing the two rings 73 together, with the circular mesh screens 72 sandwiched therebetween, using a solvent such as PVC cement. Preferably, the outside diameters of the rings (and the diameters of the circular mesh screens) are slightly less than the inside diameter of the conduit 42 so that the air resistor 70 can be retained in the distal end 48 of the pipe by friction or, if desired, by a solvent bond. Alternatively, an airflow resistor can be constructed as illustrated in FIG. 3 with one, or both, of the rings 73 threaded on their outside surfaces, glued together with the circular mesh screens 72 sandwiched therebetween, and removably received in corresponding threading on the inner surface 46 of the conduit 42 at its distal end 48.

The airflow resistance of the various blanket models can be simulated by selection of an airflow resistor. In this regard airflow resistors of varying resistance can be formed integrally with respective conduits; alternatively, a single conduit with a threaded distal end can be provided as described above to receive a threaded airflow resistor having a selected airflow resistance that simulates the airflow resistance of a particular inflatable thermal blanket.

Those skilled in the art will appreciate that the airflow resistor can be constructed in many ways. For example, a plurality of woven or non-woven fabrics can be used in place of the circular mesh screens. Alternatively, a disk of open cell type foam material can be employed. The inventor has also built airflow resistors using a plurality of small diameter tube sections, such as soda straws, packed into a honeycomb pattern. Prefabricated plastic or metal honeycomb material may also be used for airflow resistor construction. Aluminum honeycomb is available from, for example, Plascore, Inc., Zeeland, Mich. Manifestly, any cross-sectional geometry can be employed both for the small tubes and for the packing pattern of the tubes.

Figure 5:
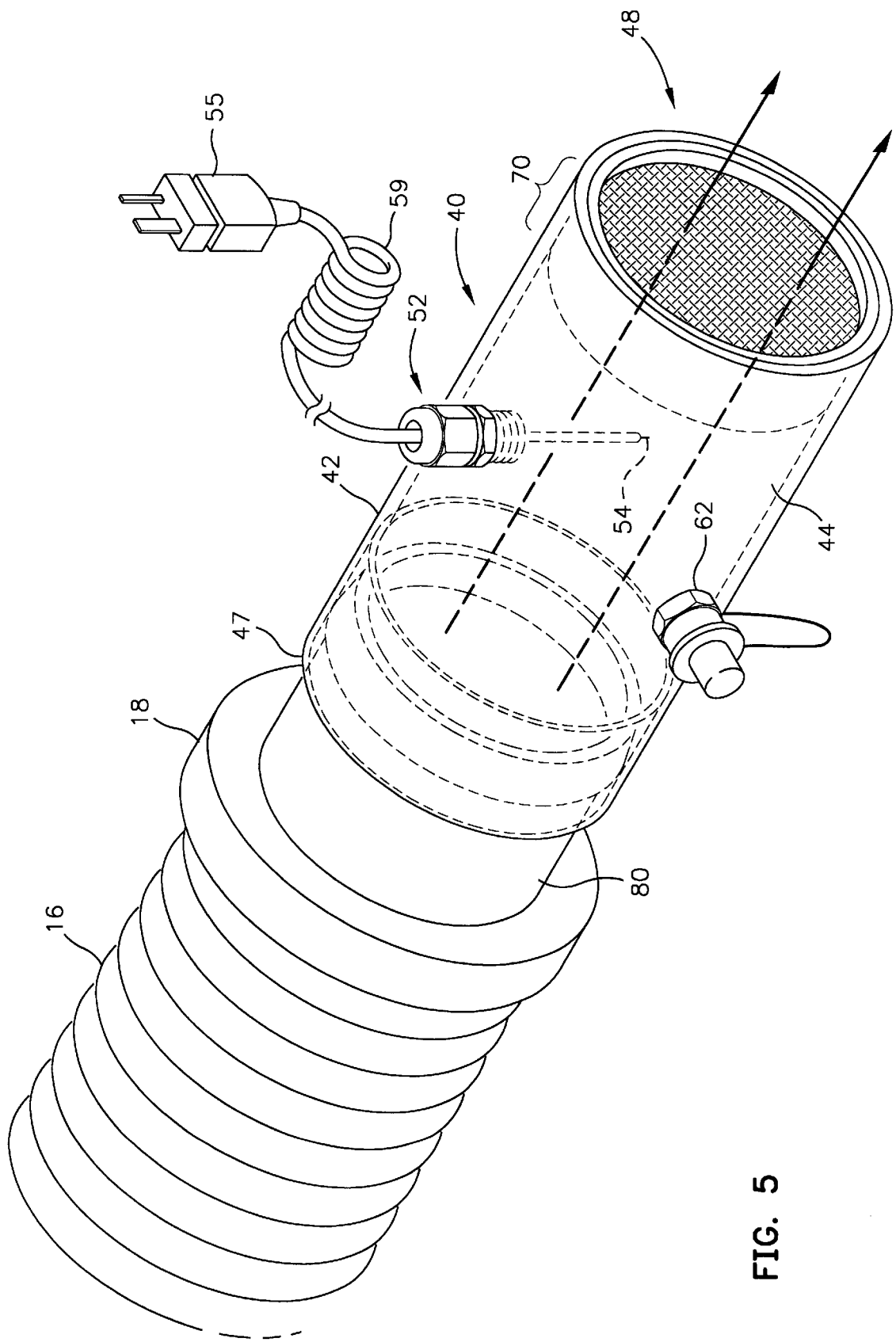

FIG. 5 shows the simulator 40 (assembled with the temperature sensor 52 and airflow resistor 70) received on a nozzle 80 conventionally attached to the distal end 18 of the air hose 16. In FIG. 5, the end of the nozzle 80 is received and frictionally retained in the proximal end 47 of the conduit 42.

With reference to FIGS. 2 and 5, measurement of the airflow temperature delivered by the air source 10 through the air hose 16 at the distal end 18 of the air hose can be understood. In this regard, the method tests the air source, specifically the temperature at which it delivers an airflow, by simulating an inflatable thermal blanket by means of the airflow resistor 70. In the method, the first end 17 of the air hose 16 is coupled to the air source 10 through the coupling 14. The simulator 40 is attached to the distal end 18 of the air hose and the air source 10 is brought to operation at a selected airflow and selected temperature. While the airflow resistor 70 presents an airflow resistance that simulates the airflow resistance of an inflatable thermal blanket, the temperature of the airflow at the distal end 18 of the air hose 16 is measured by means of the temperature sensor 52. At the point where the thermocouple bead 54 is positioned (substantially the center of the conduit 42) the temperature flowing through, and from, the air hose 16 is measured. Manifestly, the point where the temperature is measured is near the distal end of the air hose, which is the location at which an inflatable thermal blanket would receive the heated airflow. In view of the teachings given above with respect to selection of an airflow resistance to simulate a particular inflatable thermal blanket, the step of coupling the simulator 40 to the distal end 18 of the air hose 16 may be preceded by the step of selecting an airflow resistor having a value of airflow resistance corresponding to the inflatable thermal blanket to be simulated. In addition to measuring temperature of the airflow, the pressure of the airflow near the distal end 18 of the air hose 16 can be measured by attachment of a pressure line to the port 62 and connection of the line to a pressure measurement device, such as a manometer.

Figure 6:
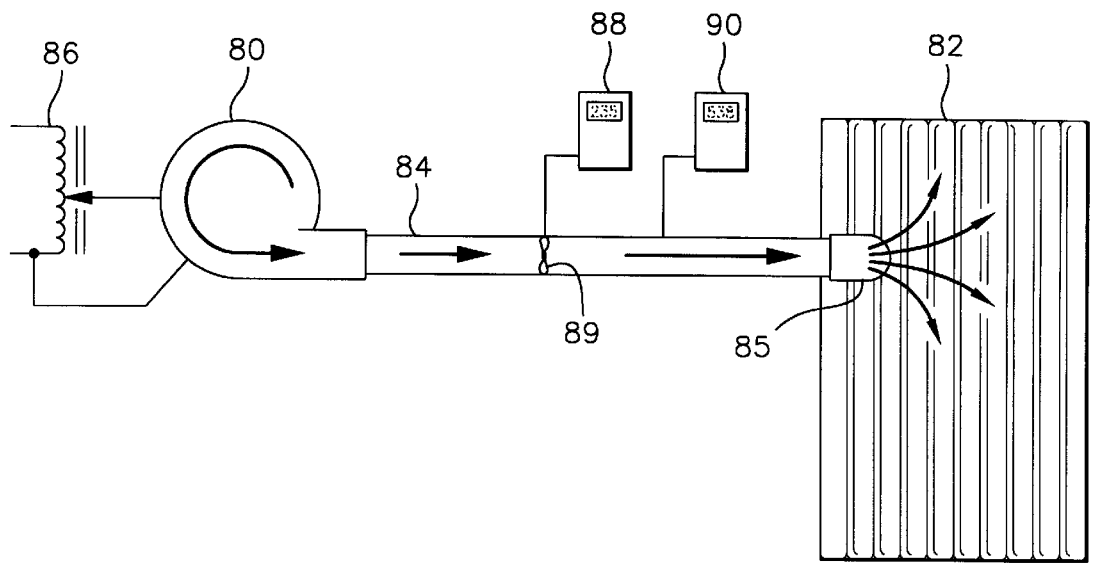
FIG. 6 illustrates a test set up to measure the airflow resistance of an inflatable thermal blanket; and, FIG. 7 illustrates a typical airflow resistance curve obtained by measuring an inflatable thermal blanket with the test setup of FIG. 6.

The airflow resistance of an inflatable thermal blanket may be measured by a test setup such as the setup illustrated in FIG. 6. In FIG. 6, a blower 80 provides an airflow to an inflatable thermal blanket 82 through an air hose 84 having two ends, one of which is coupled to the blower 80 and the other of which is coupled to a cuff 85 that defines an inflation inlet of the inflatable thermal blanket 82. An autotransformer 86 is conventionally connected to the motor of the blower 80 in order to vary the blower speed, and therefore the rate of airflow provided by the blower 80. Two instruments, an anemometer 88 and a manometer 90 have respective sensors that are disposed in the air hose 84 in order to measure the airflow velocity and pressure, respectively, within the air hose 84. In this regard, a vane 89 is positioned in the air hose 84 and conventionally coupled to the anemometer 88, which enables the anemometer 88 to measure the airflow velocity and compute the flow in standard cubic feet per minute (SCFM), where standard conditions are: 1 atmosphere, 70° F. Importantly, the sensor that enables the manometer 90 to measure pressure in the air hose 84 is positioned between the anemometer sensor 89 and the inflatable thermal blanket 82. Preferably, the manometer sensor should be as close as possible to the inflatable thermal blanket 82 in order to reduce the contribution to airflow resistance of the air hose 84.

Figure 7:
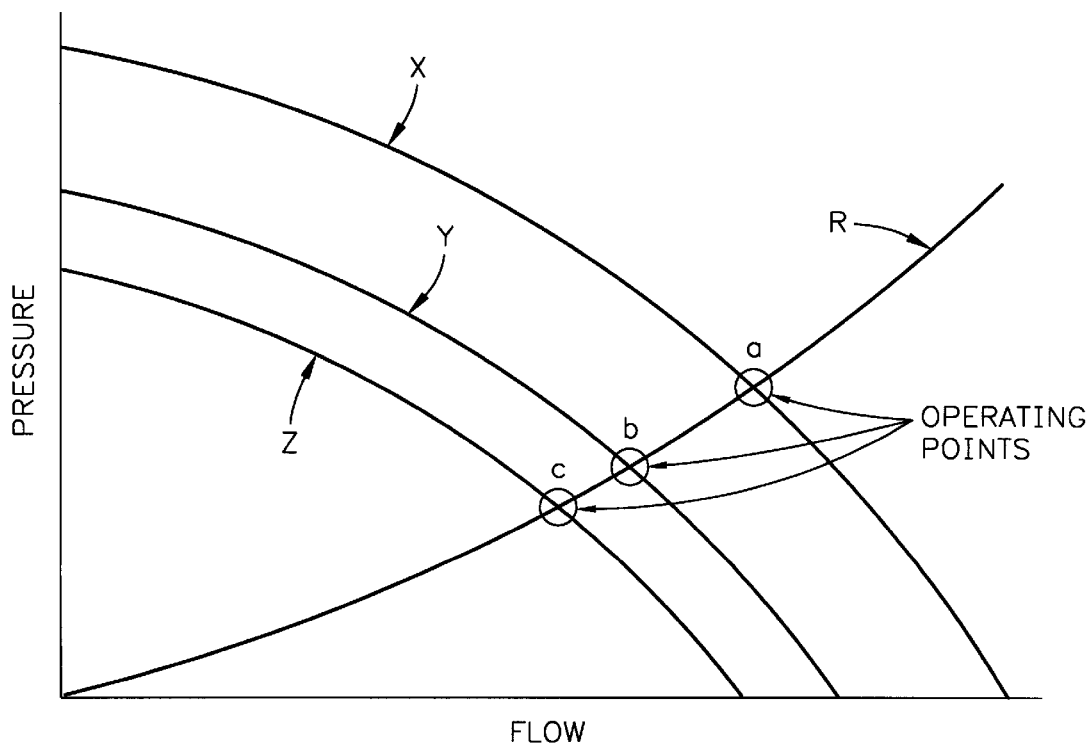

A typical set of resistance curves for three blower speed settings is presented in FIG. 7. In FIG. 7, airflow SCFM is plotted against measured pressure in inches of water (inH$_2$O). Each of the three blower curves (X, Y, and Z) in FIG. 7 illustrate the response of a blower having a fixed speed when airflow resistance is varied. For example, consider the replacement of the inflatable thermal blanket 82 in FIG. 6 with a variable airflow resistor. Assume that the speed of the blower 80 produces the blower curve depicted by X and the resistance of the variable airflow resistor is varied between zero and a maximum value. Manifestly, at the maximum airflow resistance value, no airflow will be measured, while the greatest pressure will be evident, while at the lowest airflow resistance value, the airflow will be greatest and the pressure minimal. Now, consider replacement of the variable resistance airflow resistor with the inflatable thermal blanket 82. In this test set configuration, the blower speed is varied from minimum to maximum, while the airflow characteristics of the inflatable thermal blanket 82 remain fixed. The curve of blanket resistance (R) exhibits a direct relationship between airflow and pressure. The curve R of blanket resistance intersects the blower curves X, Y, and Z at locations that may be considered the operating points of the inflatable thermal blanket 82 in response to fixed speed blowers X, Y, and Z. The airflow resistance values in Table I were obtained using the test setup illustrated in FIG. 6, with the values representing an average resistance over three fixed blower speeds.

Advantageously, the simulator described and illustrated in this application may be used in the factory and in the field to test and calibrate air sources. In this respect, when connected to one end of an air hose, the airflow resistance of any inflatable thermal blanket may be presented to an air source. The air source would be connected to the second end of the air hose and turned on to a preselected airflow rate and temperature. While operating, the speed and temperature of the airflow delivered by the air source would be adjusted to specified standard values, with the certainty that the adjustments would reflect the actual conditions under which the air source is intended to operate.

TABLE I

| BAIR HUGGER ® BLANKET MODEL NO. | Airflow RESISTANCE (inH$_2$O/SCFM) | NUMBER OF CIRCULAR MESH SCREENS |
|---|---|---|
| 305 | 0.0095 | 7 |
| 300 | 0.014 | 11 |
| 525 | 0.0145 | 11 |
| 610 | 0.0155 | 11 |
| 522 | 0.016 | 11 |
| 655 | 0.017 | 11 |
| 537 | 0.0175 | 11 |
| 310 | 0.018 | 11 |
| 315 | 0.018 | 11 |
| 540 | 0.018 | 11 |
| 530 | 0.018 | 11 |
| 110 | 0.022 | 11 |
| 650 | 0.027 | 17 |
| 536 | 0.031 | 17 |

Obviously, many variations of the invention will be evident to the skilled practitioner and may be implemented without departing from the spirit or scope of this invention which is limited only by the following claims.

I claim:

1. A method for measuring temperature of an airflow for an inflatable thermal device, comprising:

coupling a first end of an air hose to an airflow source;

coupling an airflow resistor to a second end of the air hose, the airflow resistor having a value of airflow rest that corresponds to the inflatable thermal device;

operating the airflow source at a preselected airflow rate and temperature; and measuring temperature of the airflow in the air hose.

2. The method of claim 1, wherein the airflow temperature is measured near the second end of the air hose.

3. The method of claim 1, wherein the airflow temperature is measured between the first end and second end of the air hose.

4. The method of claim 3, wherein the airflow temperature is measured near the second end of the air hose.

5. The method of claim 1, wherein the inflatable thermal device is an inflatable thermal blanket.

6. The method of claim 1, further including the step of measuring the airflow pressure in the air hose.

7. The method of claim 6, wherein the step of measuring airflow pressure is performed near where said temperature is measured.

* * * * *

UNITED STATES PATENT AND TRADEMARK OFFICE
CERTIFICATE OF CORRECTION

PATENT NO. : 5,988,876
DATED : November 23, 1999
INVENTOR(S) : Albert Van Duren

It is certified that error appears in the above-identified patent and that said Letters Patent is hereby corrected as shown below:

Title page,
Item [62], please add after "5,876,428" -- , which is a division of application No. 08/697,053, filed on Oct. 19, 1996, now U.S. Patent No. 5,693,079 --.

Column 1,
Line 8, please add after "Source" -- , which is a divisional of U.S. patent application No. 08/697,053, filed on Oct. 19, 1996, now U.S. Patent No. 5,693,079 --.

Signed and Sealed this

Eleventh Day of February, 2003

JAMES E. ROGAN
*Director of the United States Patent and Trademark Office*